(12) United States Patent  
Forry et al.

(10) Patent No.: US 8,398,922 B2
(45) Date of Patent: Mar. 19, 2013

(54) HIGHLY SENSITIVE OXYGEN SENSOR FOR CELL CULTURE

(75) Inventors: Samuel P. Forry, Rockville, MD (US); Peter C. Thomas, Germantown, MD (US)

(73) Assignee: The United States of America as represented by the Secretary of Commerce, The National Institute of Standards and Technology, Washington, DC (US)

( * ) Notice: Subject to any disclaimer, the term of this patent is extended or adjusted under 35 U.S.C. 154(b) by 49 days.

(21) Appl. No.: 12/900,587

(22) Filed: Oct. 8, 2010

(65) Prior Publication Data
US 2011/0086418 A1    Apr. 14, 2011

Related U.S. Application Data

(60) Provisional application No. 61/249,719, filed on Oct. 8, 2009.

(51) Int. Cl.
*G01N 15/06* (2006.01)
*G01N 33/00* (2006.01)
*G01N 33/48* (2006.01)

(52) U.S. Cl. ............... 422/83; 422/50; 422/94; 422/97; 422/98; 422/68.1; 422/82.05; 422/82.06; 422/82.07; 422/82.08

(58) Field of Classification Search .................. 422/50, 422/83, 94, 97, 98, 68.1, 82.05, 82.06, 82.07, 422/82.08
See application file for complete search history.

(56) References Cited

U.S. PATENT DOCUMENTS

| 5,567,598 | A | 10/1996 | Stitt et al. |
|---|---|---|---|
| 6,165,741 | A | 12/2000 | Wilson et al. |
| 6,306,661 | B1 | 10/2001 | Lakowicz et al. |
| 6,610,848 | B1 | 8/2003 | Pilato et al. |
| 7,338,778 | B2 | 3/2008 | Pitner et al. |
| 7,435,578 | B2 | 10/2008 | Wikswo et al. |
| 7,507,579 | B2 | 3/2009 | Boccazzi et al. |
| 7,569,395 | B2 | 8/2009 | Havens et al. |
| 7,704,745 | B2 | 4/2010 | Baudenbacher et al. |
| 7,713,733 | B2 | 5/2010 | Cliffel et al. |
| 2004/0077075 | A1 | 4/2004 | Jensen et al. |
| 2004/0171094 | A1 | 9/2004 | Klimant et al. |
| 2005/0153276 | A1 | 7/2005 | Wikswo et al. |
| 2005/0158845 | A1 | 7/2005 | Wikswo et al. |
| 2006/0073539 | A1 | 4/2006 | Wikswo et al. |
| 2006/0199260 | A1 | 9/2006 | Zhang et al. |
| 2009/0068700 | A1 | 3/2009 | Wikswo et al. |

*Primary Examiner* — Brian J Sines
(74) *Attorney, Agent, or Firm* — Witters & Associates; Steve Witters

(57) ABSTRACT

An oxygen sensor comprising an oxygen sensing compound and configured to substantially mitigate leaching of the oxygen sensing compound from the oxygen sensor to an outer surface thereof is provided. The oxygen sensor may comprise one or more layers. A first portion of the oxygen sensor is configured to be permeable to gas and comprises an oxygen sensing material. A second portion is disposed with or on the first portion and is configured to be permeable to gas and substantially impermeable to the oxygen sensing material.

20 Claims, 11 Drawing Sheets

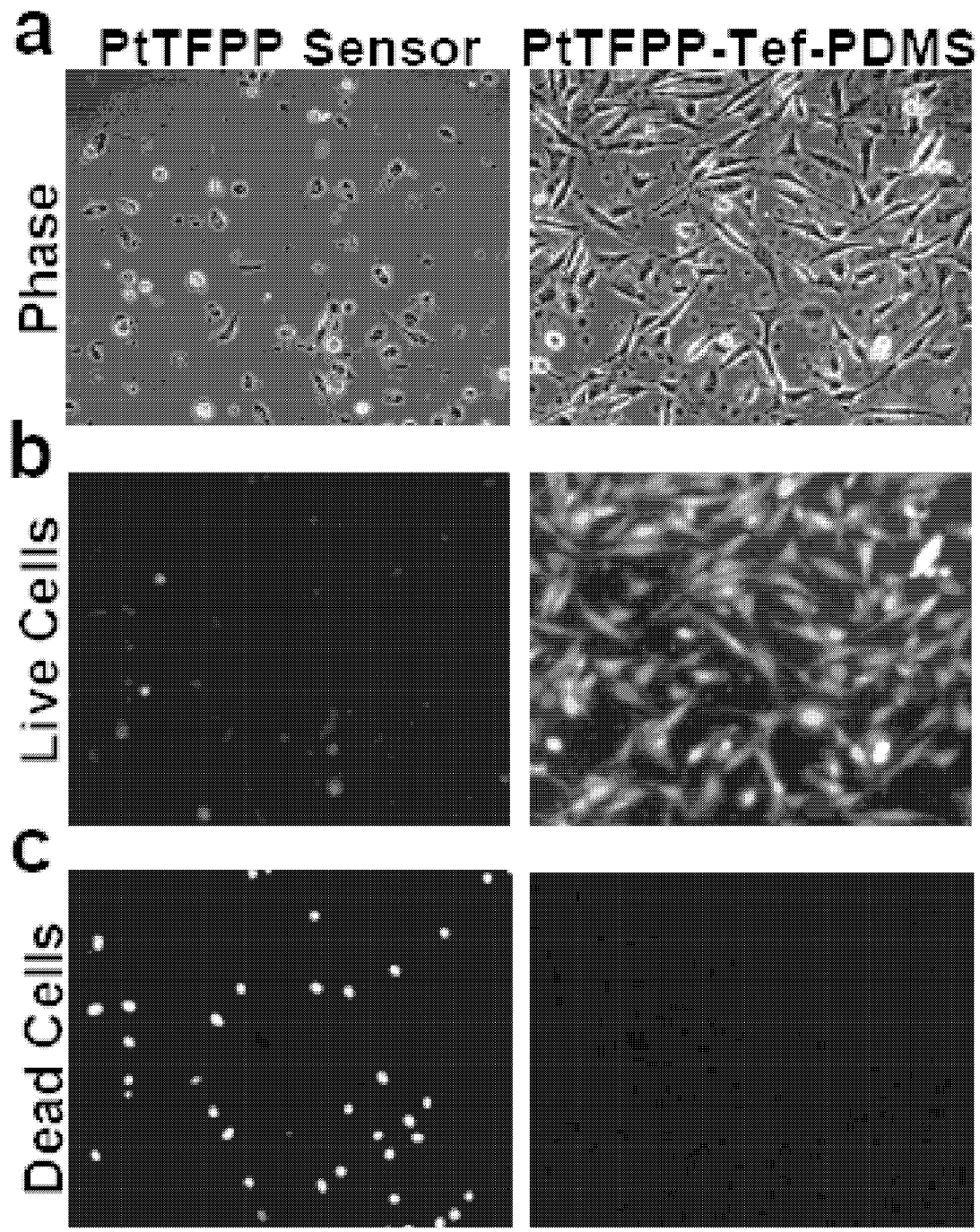
Figures 5(a-c)

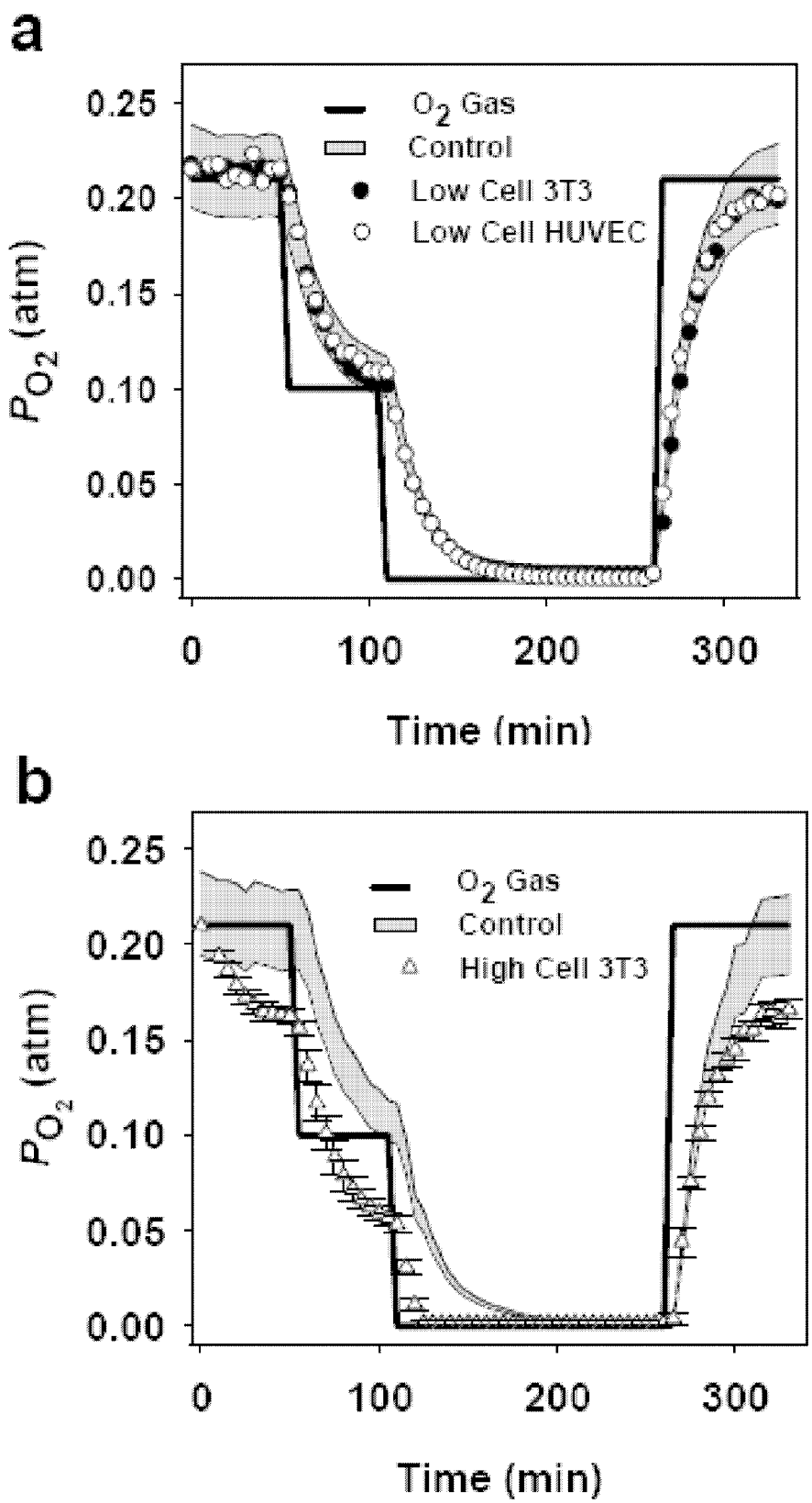
Figures 6(a-b)

HIGHLY SENSITIVE OXYGEN SENSOR FOR CELL CULTURE

CROSS-REFERENCE TO RELATED APPLICATIONS

This application claims the benefit of U.S. Provisional Application No. 61/249,719, filed Oct. 8, 2009, and is incorporated herein by reference.

STATEMENT REGARDING FEDERALLY SPONSORED RESEARCH OR DEVELOPMENT

This work is funded by the National Institute of Standards and Technology under the U.S. Department of Commerce.

FIELD OF THE INVENTION

The present invention relates to optical methods of measuring the growth of microorganisms in cultural media, and more particularly, toward methods which employ oxygen-sensing compounds.

BACKGROUND

Oxygen is a critical element to many chemical and physiological processes. Methods and apparatuses for measuring the presence and/or concentration of oxygen is important to many fields of endeavor. For example, microorganisms consume oxygen during growth, depleting the concentration of oxygen in the surrounding environment. Oxygen tension in mammalian cell culture can profoundly affect cellular differentiation, viability, and proliferation. Therefore, a measurement of oxygen in the environment surrounding a cell culture provides data on the cells in the culture.

Oxygen has been monitored with electrochemical sensors. Electrochemical sensors may allow continuous monitoring of oxygen. For example, electrochemical methods for detection of oxygen have been used in bio-reactors to insure sufficient media oxygenation. However, it may be substantially impossible to place the oxygen measurement electrode near the cells in culture to know the local conditions since the electrochemical sensors are typically too large. Electrochemical sensors are typically used in production-scale applications, and routine observation of the cells in culture is difficult if not impossible. Even when desired, electrochemical detection is not easily compatible with common microscopic integration of the cells. Also, the electrochemical approach is difficult to parallelized for high-throughput applications. Additionally, electrochemical sensors may be prone to chemical and electrical interference; they may consume oxygen; and typically have a large bulk mass. Therefore, in many applications, electrochemical sensors may be an unsatisfactory method of oxygen measurement.

Optical sensors for oxygen have overcome some of these problems associated with electrochemical sensors. Optical sensors may be based on a change in luminescence intensity emanating from phosphorescent compounds or fluorophores which are quenched with oxygen. Commercially available phosphorescent oxygen sensors typically utilize ruthenium based fluorophore to measure changes of oxygen. However, these fluorophores may lack the sensitivity to measure small changes in oxygen level due to the inherently low quantum yields. In addition, many of these fluorophores may be unstable, exhibit rapid photobleaching, and/or may load unevenly across culture dishes. Additionally, dye dispersed in aggregates may significantly compromise the ability to integrate alternative microscopy strategies such as phase contrast imaging and fluorescence imaging.

Most recently, platinum based fluorophores have been used in optical sensors to overcome some of the problems associated with the ruthenium based fluorophores. However, platinum based fluorophores may exhibit a cytotoxic effect on the growth of the cells in the culture media. The cytotoxicity of the platinum based fluorophores may thus cause the phosphorescent oxygen sensor to fail to provide desired representative data of the cell culture.

Precise measurement of dissolved oxygen in a cell culture environment in real time remains difficult. What is needed is an apparatus and method that overcomes some of the aforementioned problems associated with the prior art.

SUMMARY

In one aspect of the present invention, an oxygen sensor is provided. The oxygen sensor comprises a first layer configured to be permeable to gas and an oxygen sensing material. A second layer is disposed adjacent the first layer and is configured to be permeable to gas and substantially impermeable to the oxygen sensing material. A third layer is disposed adjacent the second layer and is configured to be permeable to gas and facilitate cell attachment therewith.

In another aspect of the present invention an oxygen sensor comprising a cytotoxic oxygen sensing material substantially homogenously dispersed within a substrate is provided.

The substrate has a permeability to oxygen of at least 500 Barrer. A barrier layer is disposed on the substrate may have a permeability to oxygen of at least 500 Barrer. The barrier layer is configured to mitigate a cytotoxic effect of the cytotoxic oxygen sensing material on a cell culture by at least 90%, during an oxygen sensing period.

In yet another aspect of the present invention, an oxygen sensor comprises a first portion and a second portion. The first portion comprises an oxygen sensing compound. The second portion is disposed on the first portion and is configured to substantially mitigate leaching of the oxygen sensing compound from the first portion to an outer surface of the second portion. The second portion is configured to have a permeability to oxygen of at least 500 Barrer.

BRIEF DESCRIPTIONS OF THE DRAWINGS

The following figures, which are idealized, are not to scale and are intended to be merely illustrative and non-limiting.

Figure 2:
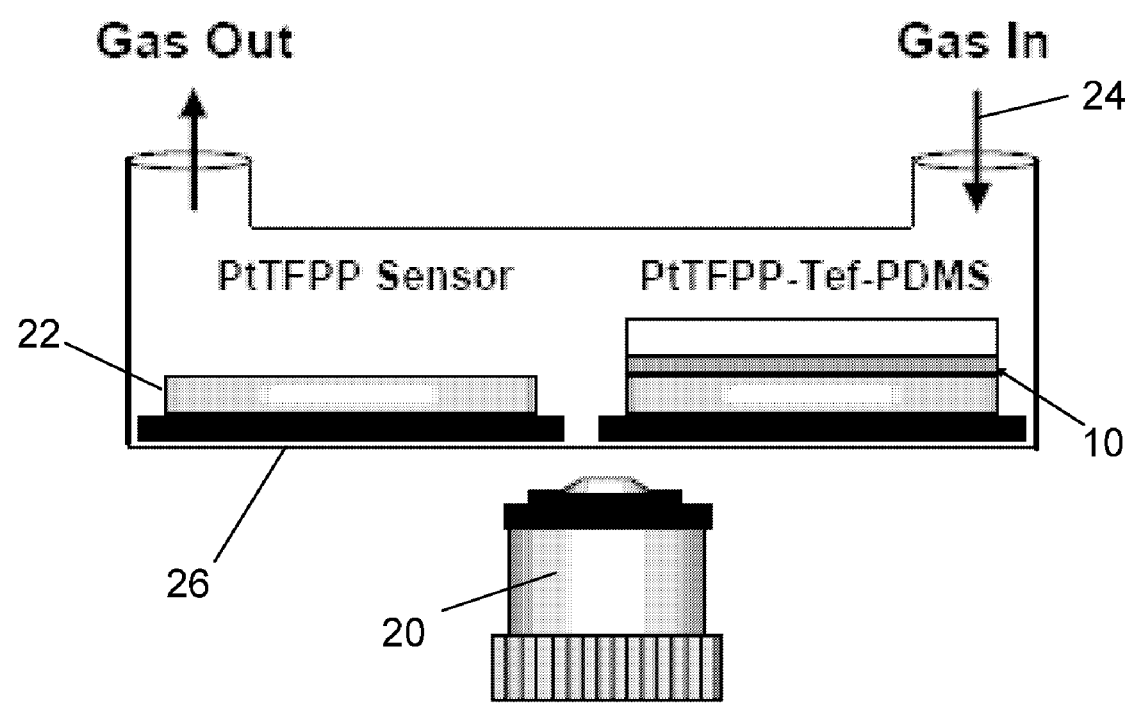
Figure 3:
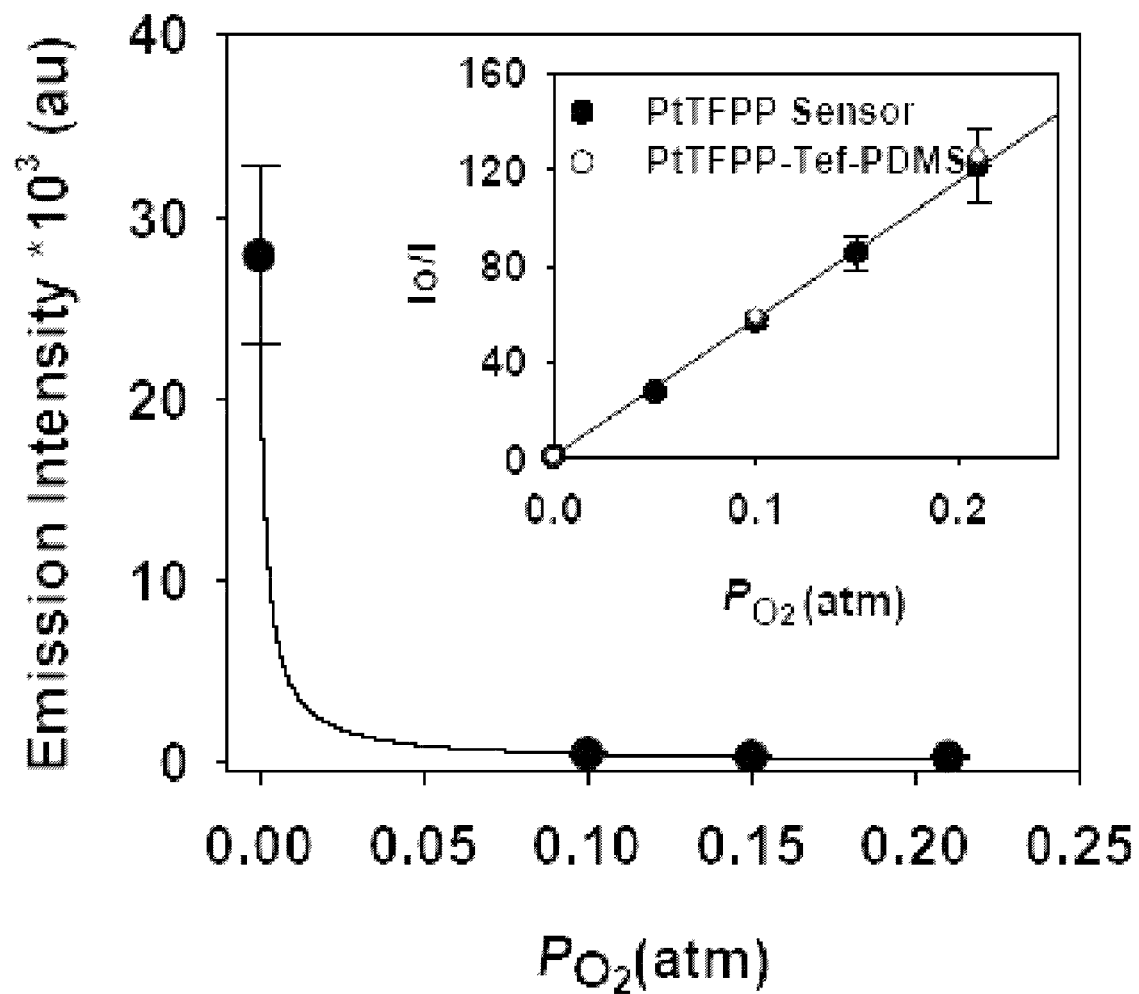
Figure 4:
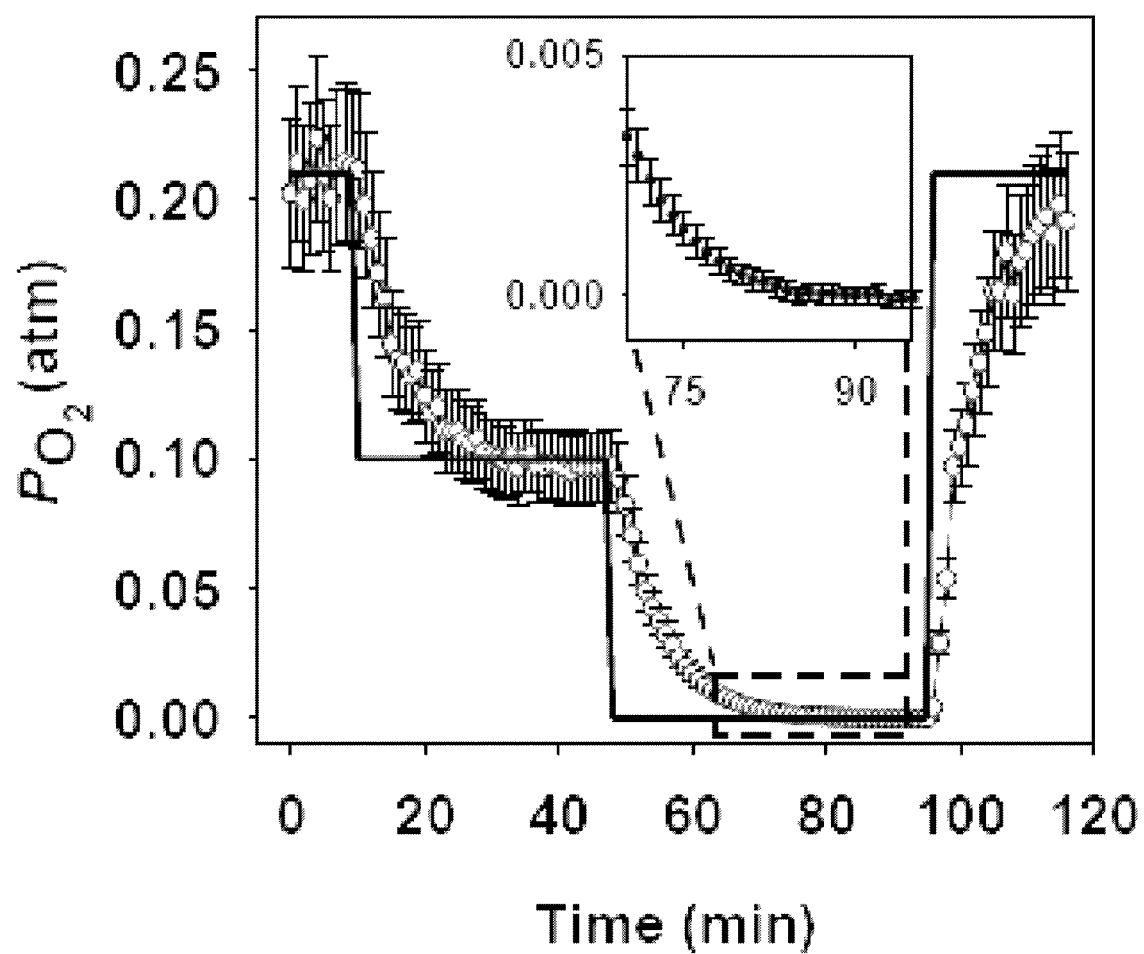
Figure 5D:
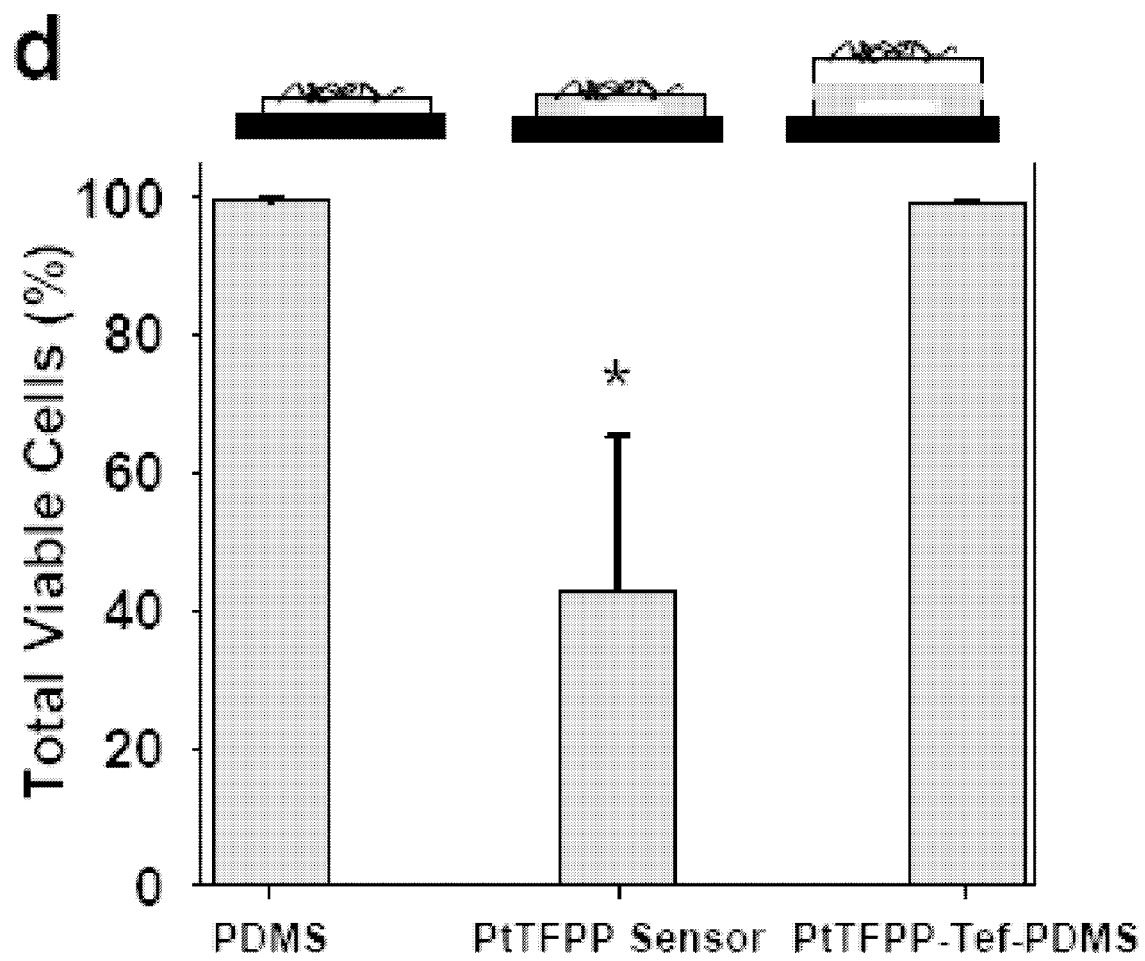
Figure 6C:
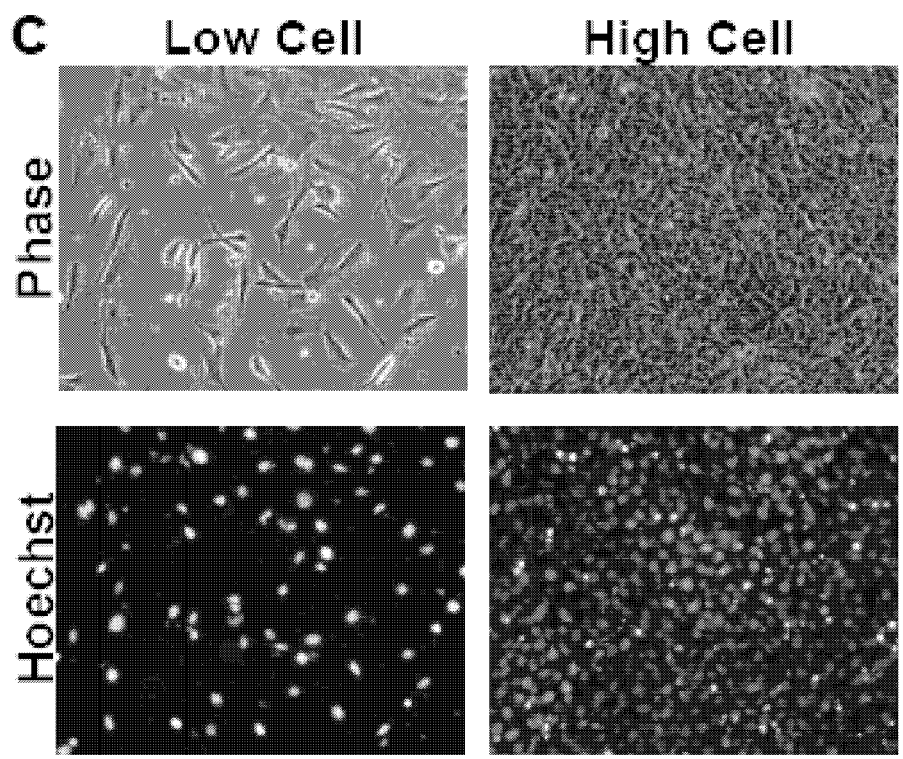
Figure 7:
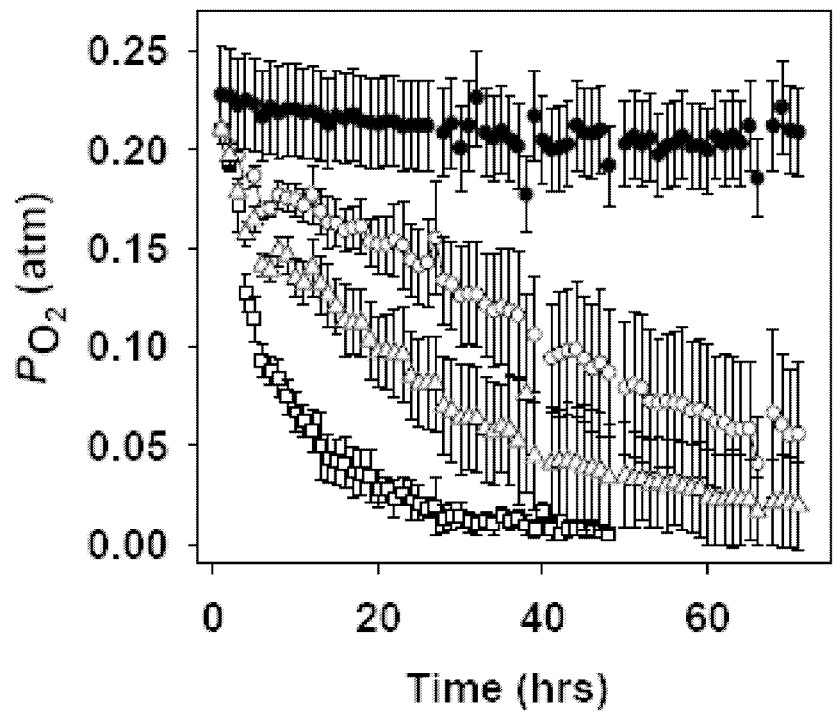
Figure 8A:
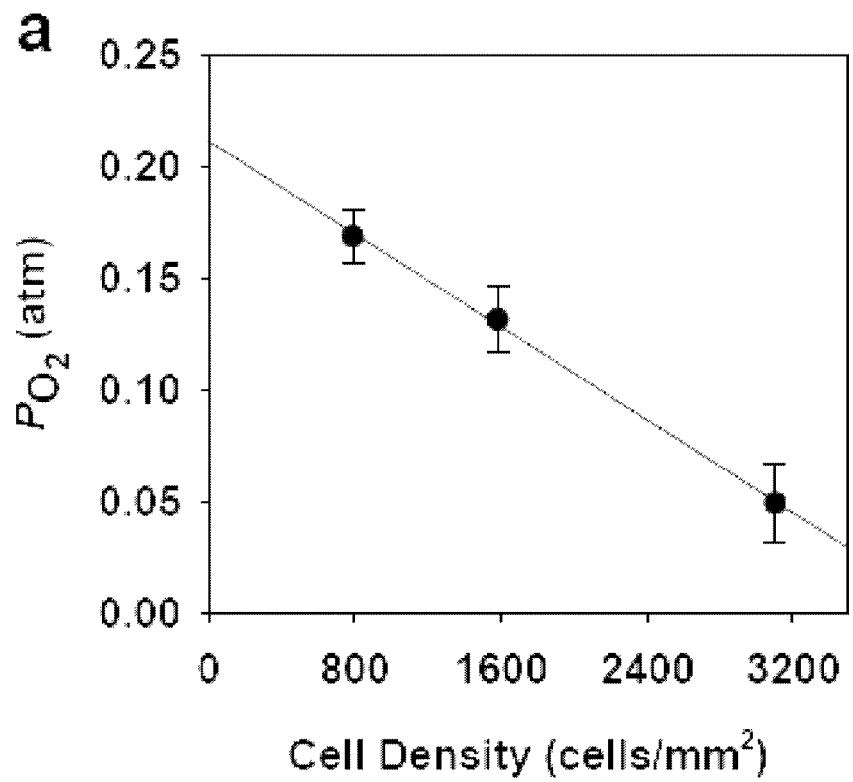
Figure 8B:
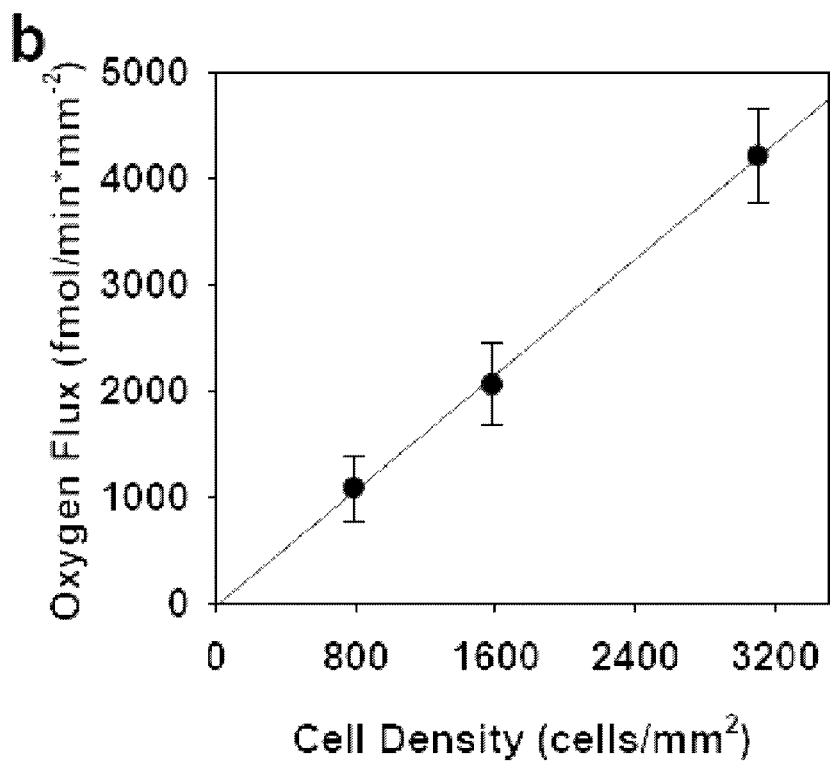
Figure 9:
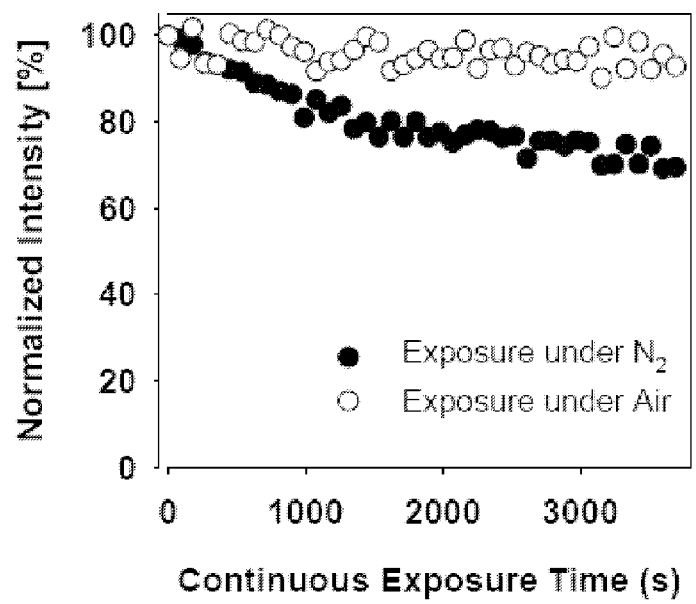
Figure 10:
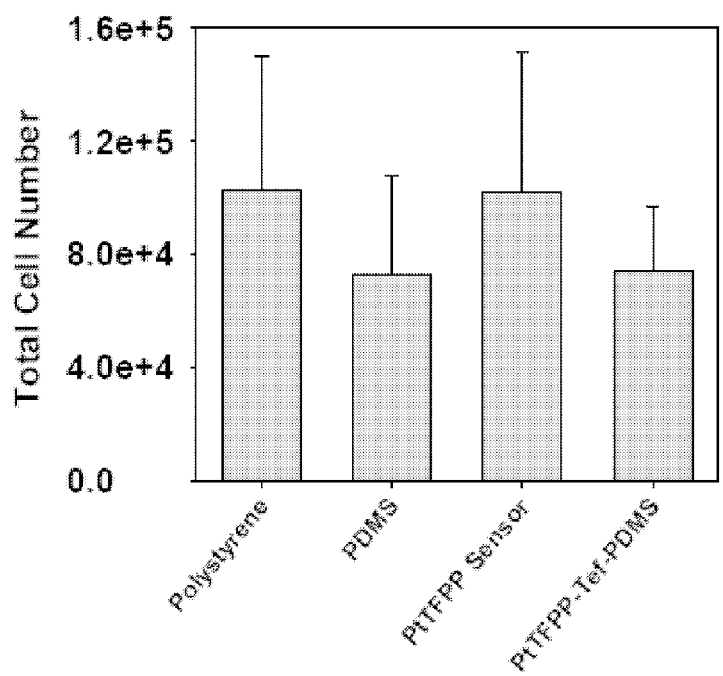
Figure 11:
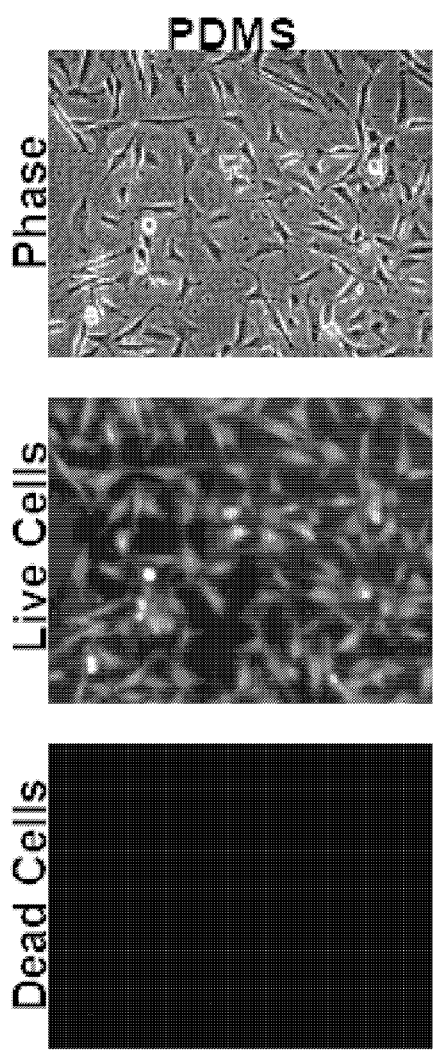

FIG. 2 schematically shows an apparatus configured for the calibration of aspects of an oxygen sensor of the present disclosure;

FIG. 3 graphically shows gas phase calibration data of a thin film PtTFPP sensor and a PtTFPP-Tef-PDMS sensor;

FIG. 4 graphically shows performance data of an oxygen sensor in cell culture medium;

FIGS. 5(a)-5(c) show images of phase contrast imaging and Live/Dead assays of cells cultured on PtTFPP and PtTFPP-Tef-PDMS sensors;

FIG. 5(d) graphically shows the phototoxicity of sensor formulations;

FIGS. 6(a) and 6(b) graphically show oxygen measurements taken with a PtTFPP-Tef-PDMS sensor wherein the sensor was in the presence of live cells;

FIG. 6(c) shows phase contrast and Hoechst nuclear stained fluorescent microscopy images of cells on a PtTFPP-Tef-PDMS sensor;

FIG. 7 graphically shows changes in measured $P_{O2}$ taken with a PtTFPP-Tef-PDMS sensor during a long term cell culture;

FIGS. 8(a) and 8(b) graphically show an effect of cell density on $P_{O2}$ and oxygen consumption;

FIG. 9 graphically shows photodegradation of a PtTFPP sensor under continuous light exposure;

FIG. 10 graphically shows proliferation of cells on various substrates;

FIG. 11 shows images of the phototoxicity of cells grown on PDMS; and

Figure 12:
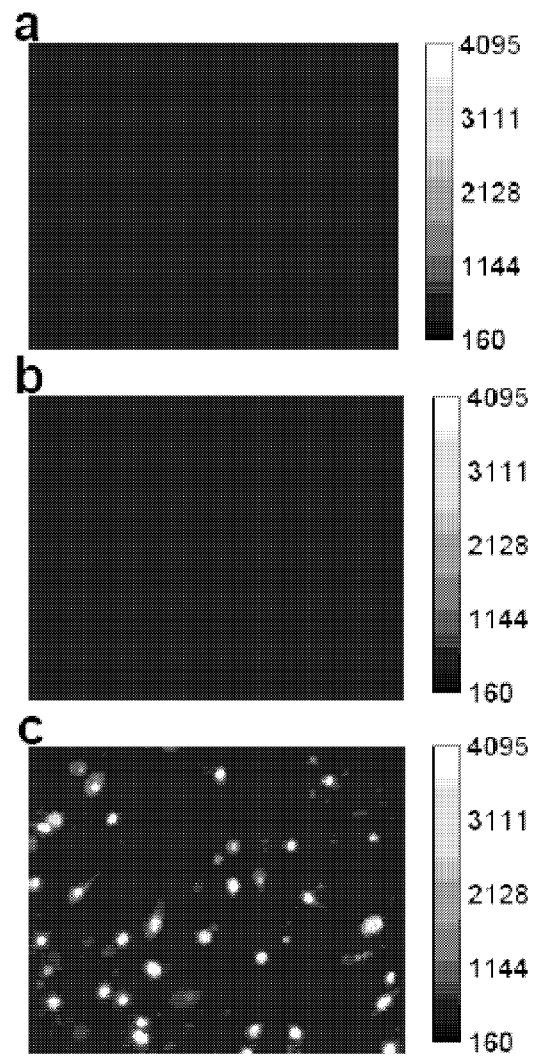

FIG. 12 shows images supporting the integration of an oxygen sensor with fluorescent cell stains.

DETAILED DESCRIPTION

Aspects of the present disclosure are directed toward highly sensitive non-invasive sensors that may accurately measure oxygen concentration in an environment of a cell culture, in real time during cell culture. Aspects of the present disclosure may be compatible with live-cell imaging techniques such as fluorescence and phase contrast microscopy. The sensed oxygen level in the cell culture environment may enable the oxygen consumption of the cells to be calculated, thus providing data on cell growth in the cell culture.

In at least one embodiment, an oxygen sensor comprises a first portion and a second portion. The first portion comprises an oxygen sensing material. The second portion may also comprise a material comprising the first portion and may be unitary therewith. Alternatively, the first and second portion may comprise different materials and may be disposed adjacent or on one another. The first portion comprises an oxygen sensing compound and the second portion is void of an oxygen sensing compound. The second portion of the sensor is configured to substantially mitigate leaching of the oxygen sensing compound from the first portion to an outer surface thereof. The oxygen sensor may be in the configuration of a thin film.

In at least one other embodiment, a non-invasive multilayer oxygen sensor for measurement of oxygen levels and oxygen consumption rate in cell culture is provided. The oxygen sensor may comprise three layers. A first layer, or lower layer, may be configured to be permeable with oxygen and provide a means for sensing oxygen. A second layer, or middle layer, may be configured to be permeable with oxygen and substantially impermeable to the means for sensing oxygen in the first layer. A third layer, or top layer, may be configured to be permeable with oxygen and facilitate cell attachment therewith. The third layer may also comprise extra cellular matrix (ECM) proteins to facilitate cell growth.

During cell culture, cells may be seeded on and attach to the third layer. As cells consume oxygen, the local oxygen concentration is altered. Due to the high oxygen permeability of each layer of the sensor, the oxygen level within the first layer of the sensor may rapidly equilibrate to reflect any change in local cellular oxygen levels. In an aspect of the disclosure where the means for sensing oxygen in the first layer is a fluorophore, changes in emission intensity from the fluorophore may allow determination of the local oxygen level around the cells and enable calculation of the amount of oxygen consumed by the cells.

Aspects of the present disclosure may provide a sensor having high oxygen sensitivity, which may be an order of magnitude more sensitive than conventional oxygen sensors and may be compatible with conventional cell microscopy imaging techniques such as phase contrast and fluorescence microscopy. Additionally, aspects of the present disclosure may substantially reduce or even eliminate any cytotoxic effects a fluorophore may have on the cell culture, allowing the use of fluorophores that may provide higher oxygen sensitivity, minimal photobleaching during extended continuous exposure, or other desired characteristics of the means for sensing oxygen. Furthermore, aspects of the present disclosure may allow facile adaption to common high throughput multi-well plate formats.

In at least one embodiment, an oxygen sensor comprises a first layer configured to be permeable to gas and configured to sense oxygen in the gas. A second layer is disposed on or adjacent the first layer and is configured to be permeable to gas and substantially impermeable to an oxygen sensing material in the first layer. A third layer is disposed on or adjacent the second layer and is configured to be permeable to gas and facilitate cell attachment therewith. This embodiment of an oxygen sensor is a multilayer sensor having adjacent layers configured to substantially reduce or eliminate any toxic or cytotoxic effects of an oxygen sensing material on a cell culture.

In at least one aspect of the present disclosure, a non-invasive multilayer oxygen sensor for measurement of oxygen levels and oxygen consumption rate in cell culture is provides. This aspect of the sensor may consist of 3 layers. The first layer being the sensing layer which comprises an oxygen sensitive fluorophore, e.g. Platinum (II) mesoTetra (pentafluorophenyl)porphine, embedded in a gas permeable polymer such as polydimethylsiloxane(PDMS). The emission intensity from the fluorophore responds to the amount of oxygen in its surrounding environment and may be characterized by the Stern-Volmer equation. As oxygen diffuses throughout the gas permeable polymer, the change of emission intensity reflects the changes of oxygen level in the environment surrounding the sensor. The second layer comprises a gas permeable glassy polymer, such as Teflon® AF, coated onto the first layer. The second layer prevents or substantially inhibits the fluorophore from leaching into the cell culture environment, but allows oxygen to diffuse therethrough quite readily. The third layer comprises a gas permeable polymer, such as PDMS, and is configured to facilitate deposition of extra cellular matrix (ECM) proteins and facilitate cell attachment onto the sensor.

In at least one other aspect of the present disclosure, a sensor incorporates an oxygen sensitive phosphorescent dye molecule, such as Platinum (II) meso-Tetra(pentafluorophenyl)porphine, substantially uniformly dispersed in a gas permeable polymer, such as PDMS. The uniform distribution of the die molecule within the polymer may allow clear visualization of attached cells through phase-contrast microscopy. In addition, fluorescent stains may be easily discriminated against the uniform background of the oxygen sensitive dye. By adapting the sensor to a high throughput multi-well plate format, routine oxygen measurement may be achieved without changing existing cell culture protocols or compromising existing culture analysis procedures. This adaption may provide additional data without added cost. A Teflon®AF, or other semi-permeable material, comprising layer is adjacent or disposed on the layer comprising the oxygen sensitive phosphorescent dye molecule and is configured to provide a barrier that substantially prevents the dye from leaching into the cell culture environment, thereby eliminating or substantially eliminating any potential cytotoxicity effects the dye may have on the cell culture. The high gas permeability of the Teflon®AF comprising layer allows the oxygen to easily diffuse through the sensor and has little or no affect on measurement capabilities. The fluorophore utilized in this aspect may have high sensitivity, up to an order of magnitude higher than existing sensors, or even higher, and may exhibit very low photobleaching, even under extended continuous light exposure. When combined with the high gas permeability of the multiple polymer layers, this sensor may provide accurate oxygen measurements for long duration cell cultures.

In at least one other embodiment, a highly sensitive oxygen sensor for cell cultures comprises three layers. A first, or lower layer, comprises an oxygen permeable material and a fluorophore. The fluorophore may be highly oxygen sensitive and/or may be toxic to the cell culture, for example the fluorophore may comprise Ru(II) complexes, Pt(II) complexes, such as Platinum (II) meso-Tetra(pentafluorophenyl)porphine, or other fluorophores configured for oxygen imaging. The oxygen permeable material in the first layer may comprise polydimethyl-siloxane (PDMS), polytrimethylsilylpropyl (PTMSP), combinations thereof, and/or other gas permeable polymers or polymeric materials, for example. The second layer is adjacent or disposed on the first layer and is configured to be substantially impermeable to the fluorophore in the first layer and substantially permeable to oxygen. For example, the second layer may comprise Teflon® AF, manufactured by DuPont™, expanded Polytetrafluoroethylene (ePTFE), Tyvek®, manufactured by DuPont™, Propore™, manufactured by 3M™, Entrant™ membranes, manufactured by Toray Industries, Sympatex® membrane, manufactured by Sympatex® Technologies, a fluoropolymer, combinations thereof, and/or other materials having desirable permeability characteristics. The third layer is adjacent or disposed on the second layer and is configured to be oxygen permeable and facilitate the deposition of extracellular matrix (ECM) proteins and the cell attachment onto the sensor. For example, the third layer may comprise polydimethyl-siloxane (PDMS), polytrimethylsilylpropyl (PTMSP), one or more polymeric organosilicon compounds, combinations thereof, and/or other gas permeable polymers, for example. Each adjacent layer is joined to adjacent layer(s), eliminating or substantially preventing gas flow between the adjacent layers.

An embodiment of the oxygen sensor of the present disclosure may comprise a multilayer sensor having adjacent layers configured to substantially reduce or eliminate any toxic or cytotoxic effects of an oxygen sensing material on a cell culture. In at least one embodiment, a highly sensitive oxygen sensor for cell cultures comprises three layers. A first, or lower layer, comprises an oxygen permeable material and a sensing material such as a fluorophore. The fluorophore may be highly oxygen sensitive and may be toxic or cytotoxic to the cell culture, for example the fluorophore may comprise Platinum (II) meso-Tetra(pentafluorophenyl)porphine (PtTFPP). The oxygen permeable material in the first layer may comprise polydimethylsiloxane (PDMS) or other gas permeable polymer, for example.

The second layer is adjacent the first layer is configured to be substantially impermeable to the oxygen sensing material in the first layer and substantially permeable to oxygen. For example, the second layer may comprise Teflon® AF, Teflon®, expanded Polytetrafluoroethylene (ePTFE), Tyvek®, or other material having desirable permeability characteristics. Desired permeability characteristics may be a high permeability to oxygen and a low permeability or substantially impermeable to the sensing material. In at least one embodiment, the sensing material senses an oxygen concentration in a fluid, gas or liquid, adjacent an upper or third layer of the sensor almost immediately upon the fluid contacting the third layer. In at least one other embodiment, the second layer is substantially impermeable to the sensing material such that any toxic or cytotoxic effects the sensing material may have on the cell culture are substantially eliminated or reduced by an amount to provide for an accurate sensing of oxygen in the fluid.

The third layer is adjacent the second layer and is configured to be oxygen permeable and facilitate the deposition of extracellular matrix (ECM) proteins and the cell attachment onto the sensor. For example, the third layer may comprise PDMS.

In one aspect of the invention, a noninvasive oxygen sensor is configured to accurately measure oxygen concentration during cell culture while being compatible with live-cell imaging techniques such as fluoroescence and phase contrast microscopy. The sensor may be prepared by integrating a porphyrin dye, e.g. Pt(II) meso-Tetra(pentafluoro-phenyl) porphine (PtTFPP) into polydimethylsiloxane (PDMS) thin films to form a first layer. Response of the PtTFPP in the presence of oxygen may be characterized by the linear Stern-Volmer relationship with high sensitivity (e.g. $K_{SV}$=584±71 atm$^{-1}$). A multi-layer sensor may be made placing a second layer adjacent or on the first layer comprising the PtTFPP-PDMS. The second layer may advantageously have a high permeability to gas or oxygen and be substantially impermeable to PtTFPP. For example, the second layer may comprise Teflon® AF. A third layer may be adjacent the second layer and comprise PDMS or other material configured to be permeable to gas or oxygen and facilitate cell attachment therewith. The multilayer sensor may effectively mitigate against dye cytotoxicity while providing a substrate for cell attachment. Using this sensor, changes in oxygen tension may be monitored in real-time as attached cells proliferated. The oxygen tension may decrease due to oxygen consumption by the cells, and the data may be analyzed using Fick's law to obtain the per-cell oxygen consumption rate. This sensor may enable new studies on the effects of dissolved oxygen on cellular behavior.

In vivo, oxygen levels may vary across a wide spectrum. For example, while atmospheric oxygen enters the lungs at an oxygen partial pressure of about 21% ($P_{O2}$=0.21 atm), the oxygen level decreases as it circulates through the body, reaching a mean oxygen level in tissue of ~3-5% ($P_{O2}$=0.03-0.05 atm). In addition, some cells may experience a dynamic oxygen environment. For example, hepatocytes in vivo may be exposed to gradients of oxygen while immune cells may encounter different oxygen levels as they migrate through different tissues. The variations of oxygen level throughout the body may significantly impact disease and wound healing processes. For instance, low oxygen levels may trigger the onset of wound healing, but prolonged hypoxia may eventually lead to non-healing wounds. Also, low oxygen levels may lead to vasoocclusion in sickle cell anemia. Additionally, cancer cells that exist in hypoxic conditions may be characterized as more virulent and more resistant to radiotherapy.

Despite the significance of oxygen tension in vivo, conventional cell culture methods typically do not specify oxygen levels and many in vitro cell cultures are performed at atmospheric oxygen levels ($P_{O2}$=0.21 atm). There are examples in the prior art where the disparity between in vivo and in vitro oxygen levels resulted in misleading conclusions. For example, in vitro studies of stem cells have demonstrated greater proliferation and reduced spontaneous differentiation at physiological oxygen tension ($P_{O2}$=0.05 atm), as well as oxygen tension-dependent differentiation pathways. Similarly the oxygen tension during cell culture has been shown to alter the intracellular redox state of T cells and to affect the response of lymphocytes toward HIV viral protein. Hepatocyte cultures must be exposed to a gradient of oxygen instead of a uniform oxygen tension in order to mimic the in vivo compartmentalization of liver. These shortcomings of current practices show a critical need to monitor and control oxygen tension in cell cultures.

During in vitro culture, oxygen is locally consumed by the cells and is replenished through equilibrium with the bulk culture medium. However, at high cell densities or long culture periods, depletion can lead to changes in bulk oxygen tension. Therefore, real time measurement strategies are needed to continuously monitor oxygen levels. Indeed, changes in the rate of oxygen consumption in cell culture may also provide a direct measurement of cellular metabolic activity.

Traditionally, the Clark electrode has been utilized to monitor oxygen. The Clark electrode is an electrode that measures oxygen on a catalytic platinum surface. However, the Clark electrode consumes oxygen during measurement and thus may alter the oxygen concentration in culture. Also, for real-time measurements, the electrode may require being placed inside the culture chamber, creating a source of contamination for the culture and complicating simultaneous imaging of the cells. Spectroscopic techniques may provide less invasive methods of measuring the oxygen tension, based on the quenching of phosphorescent molecules. For example, Ruthenium (II) complexes loaded in polymeric beads or on microplates may be used for continuous oxygen measurements. Also, oxygen probes synthesized by conjugating an oxygen-sensitive dye to macromolecular carriers (e.g. PEG or BSA) may be used to measure oxygen levels in cell culture. However, these approaches may be incompatible with imaging and these sensors may need be stand-alone, rather than integrated, measurements. In addition, low oxygen sensitivity, significant photobleaching during long culture periods, and fouling of the probes by the surrounding culture medium may limit implementation of these methods.

Aspects of the present disclosure provide a thin film polymeric sensor for making sensitive real-time oxygen measurement that may be compatible with phase contrast and fluorescence microscopy of cells. The principle of aspects of sensors disclosed herein is based on the oxygen-dependent quenching of phosphorescence from a platinum porphyrin dye embedded within a gas permeable film. In at least one embodiment, the sensor comprises a single layer. In at least one other embodiment, the sensor comprises two or more layers to provide a multi-layer sensor. Sensors of the present disclosure are configured to prevent or substantially eliminate leakage of dye into the cells and thereby substantially eliminate any issues that may be related to dye cytotoxicity, while still maintaining high sensor sensitivity.

Figure 1A:
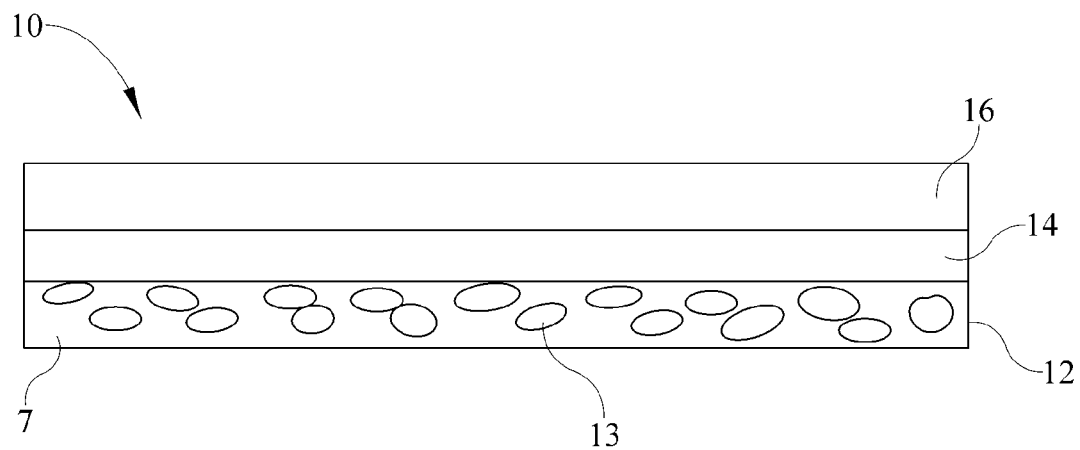
FIG. 1(a) shows a multi-layer aspect of an oxygen sensor of the present disclosure.

Shown in FIG. 1(a) is an embodiment of a multi-layer oxygen sensor 10. Multi-layer sensor 10 may be a non-invasive multilayer oxygen sensor configured for the measurement of oxygen levels and oxygen consumption rate in cell cultures. Multi-layer sensor 10 has three layers, first layer 12, second layer 14, and third layer 16.

First layer 12 comprises an oxygen sensing material 13 substantially homogenously dispersed throughout an oxygen permeable material 7, with negligible aggregation. Oxygen permeable material 7 may be configured to function as a substrate for holding oxygen sensing material 13. First layer 12 is configured to be permeable to gas and have a substantially homogenous sensing intensity. Oxygen sensing material 13 may comprises a fluorophore. Advantageously, oxygen sensing material 13 has a high sensitivity characterized with a Stern-Volmer constant of at least 500 atm$^{-1}$. In at least one embodiment, oxygen sensing material 13 comprises a fluorophore that is cytotoxic to cells to be attached with third layer 16. Oxygen sensing material 13 may comprise a Pt(II) complex such as Pt(II) meso-tetrakis(pentafluorophenyl)porphine. In at least one aspect, oxygen permeable material 7 has a permeability to oxygen of at least 500 Barrer. In at least one other aspect, oxygen permeable material 7 comprises at least one polymeric organosilicon compound such as polydimethylsiloxane. In at least one further aspect, first layer 12 has oxygen sensing material 13 dispersed, substantially homogenously and with negligible aggregation, in polydimethylsiloxane wherein it is configured to have a substantially homogenous sensing intensity.

Second layer 14 is disposed on or adjacent first layer 12 and is configured to be substantially impermeable to oxygen sensing material 13 in first layer 12 and substantially permeable to gas such as oxygen. Second layer 14 is configured to substantially reduce or eliminate any toxic or cytotoxic effects of the oxygen sensing material on a cell culture to be placed on third layer 16. In at least one aspect, oxygen sensing material 13 comprises a cytotoxic fluorophore and second layer 14 is substantially impermeable to the cytotoxic fluorophore by a degree sufficient to decrease the cytotoxicity of the cytotoxic fluorophore to the cells to be attached with said third layer by at least 90% or to a negligible level, during an oxygen sensing period. Second layer 14 may comprise a fluoropolymer and may be configured to function as a barrier layer on first layer 12. Advantageously, second layer 14 has a permeability to oxygen of at least 500 Barrer.

Third layer 16 is disposed on or adjacent second layer 14 and is configured to be gas or oxygen permeable and may be configured to facilitate the deposition of ECM proteins and the cell attachment onto sensor 10. Third layer 14 may comprise at least one polymeric organosilicon compound such as polydimethylsiloxane and may be configured to facilitate the deposition of extracellular matrix proteins therewith.

Figure 1B:
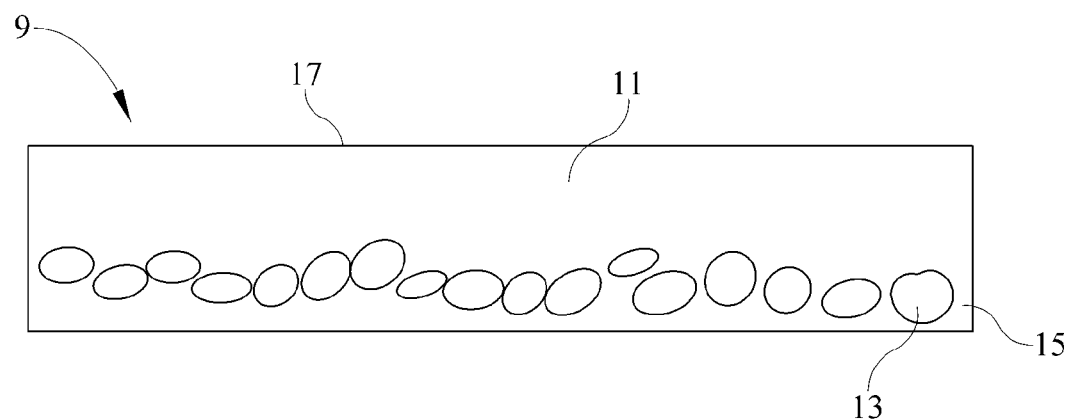
FIG. 1(b) shows another aspect of an oxygen sensor of the present disclosure.

FIG. 1(b) shows an oxygen sensor 9 comprising a film or first portion 15 and a coating or second portion 11. Oxygen sensor 9 may have film 15 and coating 11 comprising a common material and may be unitary, as shown in FIG. 1(b). In this aspect, sensor 9 comprises film 15 in a lower portion thereof and coating 11 in an upper portion thereof. Alternatively, the film and the coating may comprise different materials and may be disposed on or adjacent one another as shown in FIG. 1(a) as layers 12 and 14 respectively.

Film 15, or the lower portion of sensor 9, comprises an oxygen sensing compound 13. In at least one embodiment, oxygen sensing compound 13 comprises a fluorophore. In at least one other embodiment, film 15 comprises a polymeric organosilicon compound.

Coating 11, or the upper portion of sensor 9, is configured to substantially mitigate leaching of oxygen sensing compound 13 from film 15 to outer surface 17 of coating 11. Advantageously, coating 11 is configured to have a permeability to oxygen of at least 500 Barrer. In at least one aspect of sensor 9, coating 11 comprises a fluoropolymer.

Whether a sensor has one, two, three, or more layers, equilibration with attached cells or adjacent solution conditions may be obtained in a shorter period of time with thinner sensor layer(s). For example, a thickness of about 150 μm of multi-layer oxygen sensor 10 may provide rapid, practically instantaneous, equilibration or equilibration within a minute or less. A thin sensor may also allow facile integration with other common cell characterization strategies (e.g. microscopes, multiwell plates). In at least one embodiment, an oxygen sensor has a thickness, as defined by distance between a lower surface proximate oxygen sensing compound 13 and an upper surface, for example outer surface 17 of coating 11, of at most 500 μm. Advantageously, at least one embodiment of a sensor has a thickness between about 1 μm and 500 μm, in 1 μm increments. For example, sensor 10 may have a thickness of about 150 μm or less and sensor 9 may have a thickness of about 100 μm or less, in 1 μm increments.

EXAMPLES

Objects and advantages of this invention are further illustrated by the following examples, but the particular materials and amounts thereof recited in these examples, as well as other conditions and details, should not be construed to unduly limit this invention.

To demonstrate the utility of presently disclosed aspects of a sensor, changes in oxygen tension during long-term cell cultures for NIH 3T3 mouse fibroblasts were continuously monitored. The data was then used to calculate the per-cell rate of oxygen consumption for the example of the NIH 3T3 fibroblasts.

Cell cultures were made with human umbilical vein endothelial cells (HUVEC) (ATCC, Manassas, VA). The cells were cultured in F12K Medium (ATCC), supplemented with 0.1 mg/mL heparins (Sigma, St. Louis, MO), 0.03 mg/mL Endothelial Cell Growth Supplement (Sigma) and 10% (v/v) fetal bovine serum. NIH 3T3 mouse fibroblasts (ATCC, Manassas, Va.) were also cultured. The NIH3T3 mouse fibroblasts were cultured in Dulbecco's Modified Eagles Medium (DMEM; Mediatech, Herndon, Va.) supplemented with 10% (v/v) fetal bovine serum and the nonessential amino acids and glutamine (4 mmol/L (mM)). Both cell lines were maintained in humidified air balanced with 5% (v/v) $CO_2$ at 37° C. Unless otherwise stated, cells were maintained inside the incubator until examples began.

Cell staining was performed with Live/Dead Viability/Cytotoxicity Kit (L-3224) assay and Hoechst 33342 stain (both from Invitrogen Corporation, Carlsbad, Calif.) and were done according to the manufacturer's direction. For the Live/Dead assay, calcein AM (4 mM) and ethidium homodimer-1 (2 mM) were diluted in culture medium to get a final concentration of 1 and 4 μM, respectively. Cells were washed with phosphate-buffered saline (PBS) twice, and the stain solution was added. Cells and stain were then placed in the incubator for 30 min before being imaged. For nuclear staining with Hoechst 33242, the dye was dissolved in DMEM and an equivalent volume of dye solution was added to each cell culture well resulting in a concentration of 2 μg/mL Hoechst 33342. Cells were imaged without rinsing after 15 min of incubation with the staining solution.

Example 1

Two oxygen sensor compositions were prepared. The first sensor consisted of the porphyrin dye Pt(II) meso-Tetra(pentafluorophenyl)porphine (PtTFPP, Frontier Scientific Inc, Logan, Utah) dissolved in toluene and thoroughly mixed with a 10:1 ratio of polydimethylsiloxane prepolymer:curing agent solution (PDMS, Slygard 184; Dow-Corning, Midland, Mich.) and spin coated onto 18 mm glass coverslips. Toluene was allowed to evaporate overnight while the polymer cured. The final PtTFPP sensor film had a dye concentration of 1 mM and was 66 μm thick. The second composition consisted of a three layer sensor (PtTFPP-Tef-PDMS) prepared by spin coating Teflon® AF (Dow Chemical) onto the PtTFPP sensor films described previously and allowing solvents to evaporate overnight. Finally, an additional film of PDMS without dye was spin coated and cured on top of the Teflon® AF. All sensor formulation covered the entire surface of the coverslip with an area of 2.54 $cm^2$. The final thickness of the PtTFPP-Tef-PDMS film was approximately 150 μm. Sensor thickness was measured using an optical profiler (WYKO NT100 DMEM; Veeco, Tucson, Ariz.). Sensors were stored in the dark and used within 2 weeks of being made; new sensors were used for each example. The fabrication strategy (spin coating sequential sensor layers) may be rapidly adapted to a variety of sensor geometry. This sensor formulation was used consistently throughout these examples.

Example 2

The sensors were then calibrated in a multi-well dish as shown in FIG. 2. Calibration of the PtTFPP sensor 22 and PtTFPP-Tef-PDMS films 10 was accomplished by placing inside a multi-well dish 26 modified to allow continuous gas flow as shown in FIG. 2. Gas 24 (0%, 5%, 10%, 15%, or 21% $O_2$ in $N_2$; Scotts Specialty Gas; Plumsteadville, Pa.) was continuously introduced while the PtTFPP emission intensity was captured using a 10x (0.3NA) objective on an inverted microscope (Zeiss Axiovert 200, Thornwood, N.J.) 20 with the focus placed on the surface of the sensor as shown in FIG. 2. The films were illuminated with an X-Cite metal halide light source (EXFO, Ontario, Canada) at 546±6 nm and the emission was captured using a 580 nm dichroic and a Color IEEE-1394 camera (Scion Corporation, Frederick, MD) with an integration time of 70 ms using a long pass emission filter with a 590 nm cutoff.

All images were analyzed using NIH ImageJ (http://rsbweb.nih.gov/ij/) software. Blank PDMS films (without PtTFPP) spun to the same thickness as the oxygen sensors were also imaged to account for background intensity. These intensity values were subtracted from all sensor images in order to obtain the actual intensity from the dye itself. To determine the sensor response, $K_{SV}$ was calculated from a linear regression using the Stern-Volmer equation. The reported $K_{SV}$ and standard deviation were determined from 29 positions on 14 different sensors. To measure the dissolved oxygen in solution, culture medium without phenol red was added on top of the oxygen sensor, and gas was introduced as described above to control the headspace composition.

The sensor having PtTFPP dissolved in a gas permeable PDMS polymer matrix that was spin coated to form thin film oxygen sensors, herein after referred to as PtTFPP sensor. This thin film geometry allowed rapid diffusion of oxygen throughout the dye-filled matrix. As expected, the phosphorescence from PtTFPP sensor was significantly quenched in the presence of oxygen gas as shown in FIG. 3. The quenching response followed the Stern-Volmer equation:

$$\frac{I_0}{I} = 1 + K_{SV} \cdot [P_{O2}] \quad (1)$$

where I is the phosphorescence intensity, $I_0$ is the intensity in the absence of oxygen, $K_{SV}$ is the Stern-Volmer constant and $P_{O2}$ is the partial pressure of oxygen in the gas phase. Thus, a plot of $I_0/I$ vs. $P_{O2}$ follows a straight line as shown in FIG. 3. From the slope, $K_{SV}=584\pm71$ $atm^{-1}$ (mean and standard deviation of 14 different films). The sensor response may be less reproducible at higher oxygen level where significant quenching results in low emission intensity, as is evidenced by the relative large error bars at atmospheric oxygen conditions. However, this $K_{SV}$ value is much higher than values reported for other dyes, yielding a sensor with greater sensitivity than previously known formulations.

In the second sensor formulation, thin layers of Teflon® AF and PDMS without dye were spin coated on top of the PtTFPP sensor (the resulting sensor is denoted as PtTFPP-Tef-PDMS). The presence of the thin Teflon® layer did not alter the response of PtTFPP-Tef-PDMS sensor towards oxygen compared to the PtTFPP sensors (FIG. 3, open circles), but did sequester the dye away from the sensor surface. For both sensor formulations, equilibrium was faster than the time required to change the headspace gas composition (<1 min), reflecting the high permeability of both Teflon® AF (1500 Barrer) and PDMS (800 Barrer).

FIGS. 2 and 3 show gas phase calibration of the thin film PtTFPP and PtTFPP-Tef-PDMS oxygen sensors. The setup for acquiring $P_{O2}$ measurements on an inverted microscope at controlled gas compositions is shown schematically in FIG. 2. The phosphorescent oxygen sensors exhibited significant quenching in the presence of oxygen as shown in FIG. 3, and followed the Stern-Volmer equation with high linearity and sensitivity ($K_{SV}$=584±71 atm$^{-1}$). Black circles in FIG. 3 represent PtTFPP sensors (n=4) and open circles represent PtTFPP-Tef-PDMS (n=10) films. Data points indicate the mean values from the sensor films with standard deviations given by the vertical error bars; solid lines indicate the best fit to the data using the Stern-Volmer relationship.

Previous oxygen sensors based on the quenching of ruthenium complexes exhibited lower $K_{SV}$ values (0.2–40 atm$^{-1}$) and were confounded by issues of dye aggregation. Those dyes were relatively polar and ionic leading to low solubility and aggregation in nonpolar polymer matrices (e.g. PDMS). Dye aggregation has been associated with high variability in oxygen response, non-linear Stern-Volmer plots and uneven background emission that limits integration. In comparison with previous dyes, the PtTFPP dye was relatively nonpolar and readily dissolved in the PDMS polymer matrix without dye aggregation or phase separation. As a result, the PtTFPP-based sensors exhibited a homogenous intensity and its response to $P_{O2}$ levels followed the Stern-Volmer relationship. Additionally, no significant photobleaching effects were observed even during continuous illumination for >3600 s, as shown in FIG. 9.

FIG. 9 shows photodegradation of oxygen sensor under continuous light exposure. PtTFPP sensor under continuous exposure of phosphorescent excitation for 3600 seconds in Air (open circles) showed negligible photobleaching effects and in pure N2 (closed circles) showed a reduction of intensity by 30%. Images were taken every 90s. All images were normalized against the first image of the data set. During $P_{O2}$ measurements, only a 70ms exposure was required. Even for the longest oxygen measuring experiments (3 days), the total integrated sensing time was less than 10 s.

The sensors were then prepared for cell culture. The oxygen sensor was bonded to the inside of a 12 well cell culture plate with 0.5 µL of PDMS. Prior to cell seeding, the sensor was cleaned with 70% ethanol and rinsed with PBS. Bovine fibronectin solution (Sigma, St. Louis, Mo.) was diluted with PBS to 25 µg/mL and added to the culture well for 1 hr. to facilitate cell attachment. The fibronectin solution was aspirated and freshly trypsinized cells (HUVEC or NIH 3T3) were subsequently seeded on the fibronectin-coated sensor.

The PtTFPP sensor was placed at the bottom of a multi-well dish filled with cell culture medium. The oxygen partial pressure within the multi-well dish headspace was decreased in steps. After each step, the amount of dissolved oxygen in solution gradually decreased as it equilibrated with the controlled headspace composition. The rapid PtTFPP sensor equilibration (<1 min) allowed this transient behavior in solution to be monitored in real time as shown in FIG. 4.

FIG. 4 shows the performance of the oxygen sensor in cell culture medium. The oxygen tension in solution was measured (open circles) following step changes in the headspace gas composition (solid trace). The inset shows that the oxygen level in solution eventually decreased to 0 atm (within error) when pure $N_2$ was present in the headspace. Vertical error bars indicated the standard deviation in $K_{SV}$ and $T_0$ used to calculate $P_{O2}$.

The sensor calibration yields a gas phase oxygen partial pressure even though it is the dissolved oxygen in PDMS that actually quenches the PtTFPP dye. This calibration assumes that the sensor equilibrates rapidly with adjacent medium so that the oxygen concentration in the PDMS is always proportional to the $P_{O2}$ in the gas phase. For solution phase measurements, the rapid sensor equilibrium ensures accurate measurement of dissolved oxygen in solution. However, the calculated oxygen level reports the gas phase $P_{O2}$ (in atm) that would yield an identical oxygen concentration (in mol/L) at equilibrium. This is verified in FIG. 4 when the solution was allowed to equilibrate, and the resulting oxygen measurement matched the headspace oxygen. These units are interchangeable using the Henry's Law Constant for oxygen in water ($H_{O2\ in\ H2O}$=933L·atm/mol at 37° C.). The gas phase $P_{O2}$ was used here even for aqueous phase measurements as is conventional for reporting oxygen tension.

Example 3

The cytotoxicity of the PtTFPP on cell culture was determined. NIH 3T3 cells were seeded at 60 cells/mm$^2$ on fibronectin treated films and allowed to attach overnight in 1 mL phenol red free culture medium to minimize background fluorescence. Cells were exposed to fluorescent excitation light with an integration time of 70 ms every 15 min for 3.5 hr. Live/Dead cell assays were performed as described above on PDMS, PtTFPP sensors, and PtTFPP-Tef-PDMS and 5 positions were selected and imaged, with all conditions evaluated in triplicate. Live cells were imaged and counted with an excitation wavelength of 470 nm and emission of 540 nm. Dead cells were imaged and counted using a filter cube with excitation at 546 nm and emission at 590 nm. Total viable cells were reported by dividing the number of live cells over the total cell count for each position.

$O_2$ measurements in cell culture were made. NIH 3T3 or HUVEC cells were seeded on sensors prepared for cell culture and allowed to attach over night in 1 mL of culture medium without phenol red. Cells were placed on an inverted Axiovert 200M microscope (Zeiss, Thornwood, N.J.) with an automated stage (Ludl, Hawthorone, N.Y.) and maintained at 37° C. in a microscope incubator (In Vivo Scientific) attached to the microscope.

Initially, the $P_{O2}$ in the headspace above the cell culture medium was controlled as described in the sensor calibration example. For subsequent tests during extended cell culture, cells were maintained on the microscope throughout the test. The culture headspace was maintained with humidified 5% $CO_2$ in balanced air (In Vivo Scientific) and maintained at 37° C. as described above. Cells were cultured in 3 mL of culture medium without phenol red. Image capture began immediately after seeding. Prior to the start of each test, 3 positions were selected in each well. All tests were performed in triplicate; control wells contained medium without cells. Under these conditions, the doubling time of NIH 3T3 cells was ~20 hrs. Cell viability assays were performed with NIH 3T3 cells to identify any potential cytotoxic effects with the sensors. All sensor films were coated with fibronectin to facilitate cell attachment. In the absence of illumination, cells proliferated as well on the PtTFPP-based sensors as on polystyrene culture dishes as shown in FIG. 10. FIG. 10 shows proliferation of cells on various substrates. NIH 3T3 mouse fibroblasts were seeded (60 cells/mm$^2$) on 4 different fibronectin coated surfaces (polystyrene, PDMS films, PtTFPP sensor and PtTFPP-Tef-PDMS sensor) and allowed to proliferate for 70 hrs in the incubator (in darkness). Cells were subsequently trypsinized and counted. No statistically significant difference was observed between the different surfaces. Error bars depict the mean and standard deviation from triplicate tests.

However, upon exposure to phosphorescent excitation (546 nm for 0.07 s every 15 min for 3.5 hrs), cells on PtTFPP sensors were observed by phase microscopy to round up and detach as shown in FIG. 5(a). A Live/Dead assay utilizing calcein AM to stain live cells and ethidium homodimer to stain dead cells confirmed significant phototoxicity for the PtTFPP sensor as shown in FIG. 5 (b) and (c).

FIG. 5 shows the phototoxicity of sensor formulations. NIH 3T3 cells were cultured on three surfaces (PDMS, PtTFPP sensor, and PtTFPP-Tef-PDMS) exposed to 70 ms exposures of 546 nm light every 15 min for 3.5 hrs and evaluated by phase contrast imaging (a) as well as by Live/Dead assays (b,c). Significant phototoxicity was observed on the PtTFPP sensor as compared to PDMS without dye, FIG. 11, but the three-layer sensor mitigated the phototoxic effects. The percentage of viable cells was quantified for each substrate (d) and a 2-tail t-test was used to compare each sensor formulation to the PDMS without dye (* indicates $p < 0.05$). Columns and error bars indicate mean and standard deviation from triplicate tests.

Cells attached to PDMS without PtTFPP proliferated normally and no phototoxicity was observed as shown in FIG. 11. FIG. 11 shows the phototoxicity for cells grown on PDMS.

Representative phase contrast images and fluorescently labeled Live/Dead Assay images of NIH 3T3 fibroblasts grown on fibronectin coated PDMS film and exposed to 70 ms exposures of 546 nm light every 15 min for 3.5 hrs. These data provide a control set for phototoxicity evaluation of the oxygen sensor formulation.

The excited PtTFPP has been shown previously to produce reactive oxygen species (ROS) when quenched by oxygen. The short lifetime of these reactive species should preclude them diffusing out of the sensor after illumination. However, the PtTFPP dye itself may escape from the PtTFPP sensors and partition into the cell membranes, leading to ROS generation locally and the observed phototoxicity. In the second sensor formulation, PtTFPP-Tef-PDMS, phototoxicity was mitigated. Here a thin Teflon® AF layer was added on top of the PtTFPP sensor, followed by a second PDMS layer without dye. We hypothesize that while oxygen diffuses easily through the Teflon® layer, the PtTFPP would be effectively blocked due to the low diffusivity of molecules of this size through Teflon. The second PDMS layer was added to facilitate protein adsorption and cell attachment. Cells cultured on the PtTFPP-Tef-PDMS sensor, shown in FIG. 5(a), exhibited similar morphology to cells on just PDMS, shown in FIG. 11. Quantification of the Live/Dead assay confirmed that the phototoxicity was completely mitigated with the PtTFPP-Tef-PDMS formulation, FIG. 5(d).

All of the sensor films (including the non-toxic PtTFPP-Tef-PDMS formulation) were compatible with common microscope methods, allowing oxygen sensing and microscopy to be performed simultaneously. Using phase microscopy, cell motility as well as filopodia movement were easily observed through time-lapsed imaging Likewise, the fluorescence from cells stained with calcein AM and ethidium homodimer in the Live/Dead assay was easily visualized. Even though the emission wavelengths of the PtTFPP and the ethidium homodimer overlapped, the PtTFPP dye was homogenous throughout the sensor film while the cell stain was localized in the fixed cells, enabling facile discrimination, as shown in FIG. 12. FIG. 12 shows the integration of oxygen sensor and fluorescent cell stains. Representative fluorescent image of blank PDMS films showed minimal background emission are shown in FIG. 12(a). The PtTFPP sensor without cells showed an emission that was homogeneous in intensity throughout the field of view, FIG. 12(b). On the same sensor formulation, dead cells (NIH 3T3 fibroblasts) stained with ethidium homodimer generated local bright spots that were clearly visible over the PtTFPP emission, FIG. 12(c) even though the emission wavelengths of the film and stain overlapped.

It should be noted that such microscopic evaluations on cells would have been difficult or impossible to perform with previous oxygen sensor designs but were easily accomplished using the current thin film sensors.

$O_2$ was monitored during live cell culture. NIH 3T3 and HUVEC cells were seeded at very low densities on separate PtTFPP-Tef-PDMS sensors and allowed to attach and spread overnight. Subsequently, the $P_{O2}$ in the cell culture was monitored following step changes in the head space gas composition to verify that oxygen measurements could be made during active cell culture. All culture medium was replaced prior to the start of the test to ensure that the $P_{O2}$ levels in all chambers were 0.21 atm (ambient) when measurements began. The measured $P_{O2}$ levels in solution equilibrated gradually to the composition of the head space following each step change, as shown in FIG. 6(a). The $P_{O2}$ measurements for wells containing cells at low densities were not statistically different from the control wells that did not contain cells. This data confirmed that oxygen measurements could be made in the presence of cells and indicated that at low cell densities, the $P_{O2}$ levels were not affected by the cells.

FIG. 6 shows oxygen measurements in the presence of live mammalian cells. At low cell seeding density (60 cells/mm$^2$) of HUVEC (open circles) or NIH 3T3 (black circles), the $P_{O2}$ measured in culture was not statistically different from the control well (shaded region) that contained no cells, FIG. 6(a). At high cell densities (3100 cells/mm$^2$, open triangles), the measured $P_{O2}$ was significantly lower than the control throughout the test, indicating oxygen consumption by the cells, FIG. 6(b). Representative phase contrast and Hoechst nuclear stained fluorescent microscopy images of NIH 3T3 cells on the PtTFPP-Tef-PDMS oxygen sensor are shown at low and high densities, FIG. 6(c). The shaded region in FIGS. 6 (a) and (b) shows the 95% confidence interval envelope based on the uncertainty in measuring $K_{SV}$ and $I_0$. Data points and error bars in FIG. 6(b) represent means and standard deviations from triplicate tests.

When cells were plated at high densities, however, cellular consumption of oxygen lead to significant changes in solution oxygen tension, FIG. 6(b). Culture medium was again replaced at the start of the test (t=0), but in this case, $P_{O2}$ in the presence of cells quickly dropped to a level significantly lower than that in the control well without cells (from 0.21 atm to 0.16 atm over the first 50 min). Subsequently, the $P_{O2}$ in the cell culture responded to the step-changes in the headspace gas composition, and exhibited time constants that were similar to those observed in the low-density cultures or in the control well. However, the measured values of $P_{O2}$ in the high-density culture remained significantly lower than that in the headspace or the measured $P_{O2}$ in the control wells.

For the confluent cell monolayer evaluated, no spatial variation in $P_{O2}$ was observed across the field of view (1 mm$^2$). Representative phase and nuclear-stained fluorescence microscopy images allowed the different cell densities evaluated here to be observed, FIG. 6(c). These images further demonstrated the facile integration of live-cell microscopy with this oxygen sensing strategy.

During normal metabolism in culture, cells consume oxygen continuously, and the depleted oxygen is replaced diffusively from the surrounding culture medium, the culture flask head space, and/or maybe the cell culture plate material. At low cell densities, FIG. 6(a), small amounts of oxygen were consumed and diffusion was sufficient to replace the consumed oxygen, giving similar results to the control. However, at higher cell densities, FIG. 6(b), the greater number of cells consumed considerably more oxygen with a significant decrease in the local oxygen concentration compared to the control. In this case, oxygen supplied by diffusion was only able to keep up with oxygen consumption once a relatively steep concentration gradient emerged between the culture substrate and the solution surface (e.g. 0.16 atm to 0.21 atm at 50 min). Once established, this gradient was maintained throughout the test. For example, when the headspace $P_{O2}$ was brought to 0.1 atm, the measured $P_{O2}$ in the high density culture dropped to 0.05 atm. Without the direct measurements shown here, the local oxygen tension could only be roughly inferred by making assumptions about per-cell rates of oxygen consumption. Further, any changes in metabolic activity that affect the rate of oxygen consumption (e.g. in response to a novel drug treatment) may go unmonitored.

For short observation times, the rate of oxygen consumption was constant and a stable concentration gradient was observed. However, over longer observation times, cellular proliferation increases the number of cells present as well as the rate of total oxygen consumed. These effects were observed by measuring $P_{O2}$ immediately following the addition of suspended cells and repeating the measurement every hour for 72 hrs as shown in FIG. 7.

FIG. 7 shows changes in measured $P_{O2}$ during long-term cell culture. NIH 3T3 mouse fibroblasts were seeded at three densities: 790 cells/mm$^2$, 1580 cells/mm$^2$, 3100 cells/mm$^2$. PtTFPP-Tef-PDMS sensors were used to measure the $P_{O2}$ throughout three days of culture. In each case, the solution oxygen tension decreased over time relative to a control well with no cells (black circles) due to proliferation and cellular oxygen consumption. As cells proliferated over several days, oxygen tension continued to drop. Data points indicate mean $P_{O2}$ measurements from triplicate tests with the standard deviation shown by error bars. The difference between each seeding density was statistically significant (two factor ANOVA, p<0.05).

As cells sedimented and attached to the bottom of the culture dish and then proliferated over the course of the experiment, the $P_{O2}$ in solution decreased monotonically. Initially, between 0-8 hrs, the measured $P_{O2}$ decreased rapidly in all cell cultures, and the steepness of the decrease correlated with the cell density. This time frame correlated with the time required for attachment of cells to the sensor surface, and this decrease in $P_{O2}$ was attributed to the initial formation of a stable concentration gradient between the attached cells on the sensor and the surface of the culture medium. Subsequently, $P_{O2}$ in culture continued to drop, until it leveled off when approaching the limiting value of $P_{O2}$=0 atm. The above $P_{O2}$ response is consistent with constant cell proliferation followed by insufficient supply of oxygen by diffusion alone.

This example depicted the dynamic oxygen tension that can occur during long-term cell culture. For the highest cell seeding density (3100 cells/mm$^2$), the local oxygen tension after 24 h of culture was essentially zero. Thereafter, cell consumption of oxygen was limited by the rate of diffusion of oxygen from solution. Further, the specific oxygen tension was very dependent on the number of cells present. At the lower seeding densities (790 cells/cm$^2$), the oxygen level dropped throughout culture, but remained above 0.05 atm even after 72 hrs. The direct oxygen measurements shown here provided critical information regarding the state of the changing culture conditions throughout the long-term culture.

When $P_{O2}$ in culture after cells attached was compared between seeding densities, it was evident that the decrease in oxygen tension correlated with the cell density in culture, FIG. 8(a). FIG. 8 shows effect of cell density on $P_{O2}$ and oxygen consumption. Measured $P_{O2}$ at 12 hrs post-seeding was plotted against the cell density, FIG. 8(a). Fick's law was used to calculate the oxygen flux at each cell density, FIG. 8(b). The per cell rate of oxygen consumption determined from the linear regression was 1.38±0.04 fmol·min$^{-1}$·cell$^{-1}$ for the NIH 3T3 mouse fibroblasts. Data points and error bars indicate the mean values and standard deviations of triplicate tests; solid traces are linear regressions to the data.

The linearity of the relationship between $P_{O2}$ and cell density indicated that the net oxygen consumption in each case was dependent only on the total number of oxygen consuming cells. Since the cells were evenly distributed across the bottom of the well, a spatially uniform oxygen concentration gradient was assumed between the cells and the top surface of the culture medium. The oxygen flux ($J_{O2}$) that resulted was analyzed using the 1-dimensional steady state solution to Fick's Law:

$$J_{O2} = \frac{D \cdot \Delta P_{O2}}{h} \qquad (2)$$

where D is the diffusivity of oxygen in aqueous solution (3.3×10$^{-5}$ cm$^2$/s), $\Delta P_{O2}$ is the difference in oxygen partial pressure between the cell microenvironment and the culture medium surface, and h is the height of the culture medium. Using equation 2, the $P_{O2}$ measurements were used to calculate oxygen flux as a function of cell seeding density, FIG. 8(b). The slope of this data is the per-cell rate of oxygen consumption, and the linear relationship shows that this rate is independent of cell density for the conditions explored here. From FIG. 8(b), the per-cell rate of oxygen consumption for NIH 3T3 mouse fibroblasts is 1.38±0.04 fmol·min$^{-1}$·cell$^{-1}$. This value is similar to rates of oxygen consumption reported for other cell types.

Aspects of the present disclosure provide new oxygen sensor configured to quantify changes in oxygen tension during in vitro cell culture. Aspects of the oxygen sensor are based on the oxygen-dependent quenching of the phosphorescent porphyrin dye, PtTFPP, which is incorporated into a gas-permeable thin polymer film. A multi-layer sensor design, with a first layer of the PtTFPP dye in PDMS, a second layer of Teflon® AF, and a third (top) layer of PDMS with no dye, may be effective for culturing adherent cells and mitigating phototoxicity from the PtTFPP dye. A major advantage of the current thin film sensor may be that it allows facile integration of oxygen measurements with both phase contrast and fluorescence microscopy to characterize and quantify cell viability, motility and cell count. Compared to previous oxygen sensors which may have had problems associated with photodegradation and lack of sensitivity, aspects of the currently disclosed thin film sensor may have high sensitivity ($K_{SV}$=584 atm$^{-1}$) and negligible photobleaching. In situ measurements of $P_{O2}$ during cell culture revealed significant drops in local oxygen tension for high cell densities. Further, long time cultures revealed dynamic changes in $P_{O2}$ as cells proliferated. The rate of per-cell oxygen consumption calculated here for NIH 3T3 fibroblasts was consistent with reported values for other cell types. The method and apparatus disclosed herein is configured to measure oxygen tension in situ during cell culture which may enable the effects of local oxygen levels on cell behavior to be determined and provide the needed measurements for controlling this important component of the cellular microenvironment.

The invention claimed is:

1. An oxygen sensor comprising:
    a first layer configured to be permeable to gas and comprising an oxygen sensing material;
    a second layer disposed adjacent said first layer configured to be permeable to gas and substantially impermeable to said oxygen sensing material;
    a third layer disposed adjacent said second layer configured to be permeable to gas and facilitate cell attachment therewith; and
    said oxygen sensing material comprises a fluorophore.

2. The oxygen sensor of claim 1 wherein said fluorophore has a high sensitivity characterized with a Stern-Volmer constant of at least 500 atm$^{-1}$.

3. The oxygen sensor of claim 2 wherein said fluorophore is cytotoxic to cells to be attached with said third layer.

4. The oxygen sensor of claim 3 wherein said cytotoxic fluorophore comprises Pt(II) meso-tetrakis(pentafluorophenyl)porphine.

5. The oxygen sensor of claim 3 wherein said second layer is substantially impermeable to said cytotoxic fluorophore by a degree sufficient to decrease the cytotoxicity of said cytotoxic fluorophore to the cells to be attached with said third layer to a negligible level.

6. The oxygen sensor of claim 5 wherein said second layer comprises a fluoropolymer.

7. The oxygen sensor of claim 1 wherein said first layer comprises polydimethylsiloxane.

8. The oxygen sensor of claim 7 wherein said first layer comprises said oxygen sensing material in said polydimethylsiloxane substantially homogenously and with negligible aggregation, said first layer having a substantially homogenous sensing intensity.

9. The oxygen sensor of claim 1 wherein said third layer comprises polydimethylsiloxane and is configured to facilitate the deposition of extracellular matrix proteins therewith.

10. The oxygen sensor of claim 1 having a thickness of at most about 150 µm, said thickness being a distance between a lower surface of said first layer and an upper surface of said third layer.

11. The oxygen sensor of claim 1 wherein said oxygen sensing material is a cytotoxic oxygen sensing material and is substantially homogenously dispersed within said first layer;
    said first layer having a permeability to oxygen of at least 500 Barrer;
    said second layer having a permeability to oxygen of at least 500 Barrer; and
    said second layer being configured to mitigate a cytotoxic effect of said cytotoxic oxygen sensing material on a cell culture by at least 90%, during an oxygen sensing period.

12. The oxygen sensor of claim 11 wherein said cytotoxic oxygen sensing material comprises a Pt(II) complex.

13. The oxygen sensor of claim 12 wherein said cytotoxic oxygen sensing material comprises Pt(II) meso-tetrakis(pentafluorophenyl)porphine.

14. The oxygen sensor of claim 13 wherein said second layer comprises a fluoropolymer.

15. The oxygen sensor of claim 11 wherein said first layer comprises at least one polymeric organosilicon compound.

16. An oxygen sensor comprising a first layer and a second layer;
    said first layer comprising an oxygen sensing compound containing a fluorophore;
    said second layer being disposed with said first layer and configured to substantially mitigate leaching of said oxygen sensing compound from said first layer to an outer surface of said second layer; and
    said second layer being configured to have a permeability to oxygen of at least 500 Barrer.

17. The oxygen sensor of claim 16 wherein said first and second layers comprise a common material and are unitary.

18. The oxygen sensor of claim 16 wherein said first layer and said second layer comprise different materials.

19. The oxygen sensor of claim 16 comprising at least one of a), b), and c):
    a) said second layer comprises a fluoropolymer;
    b) said first layer comprises a polymeric organosilicon compound; and
    c) said oxygen sensor has a thickness of at most about 150 µm.

20. An oxygen sensor comprising a first portion and a second portion;
    said first portion comprises an oxygen sensing flurorphore; and
    said second portion is disposed with said first portion and is configured to substantially mitigate leaching of said oxygen sensing flurorphore from said first portion through said second portion.

* * * * *